US011026779B2

(12) United States Patent
Arbisser (10) Patent No.: US 11,026,779 B2
(45) Date of Patent: Jun. 8, 2021

(54) INTRAOCULAR LENS AND METHODS FOR IMPLANTING THE SAME

(71) Applicant: Lisa Arbisser, Sarasota, FL (US)

(72) Inventor: Lisa Arbisser, Sarasota, FL (US)

( * ) Notice: Subject to any disclaimer, the term of this patent is extended or adjusted under 35 U.S.C. 154(b) by 59 days.

(21) Appl. No.: 15/613,805

(22) Filed: Jun. 5, 2017

(65) Prior Publication Data

US 2017/0354494 A1    Dec. 14, 2017

Related U.S. Application Data

(60) Provisional application No. 62/348,064, filed on Jun. 9, 2016.

(51) Int. Cl.
*A61F 2/16*    (2006.01)

(52) U.S. Cl.
CPC ........ *A61F 2/16* (2013.01); *A61F 2002/1681* (2013.01); *A61F 2002/16901* (2015.04)

(58) Field of Classification Search
CPC ............... A61F 2002/16901; A61F 2002/1681
See application file for complete search history.

(56) References Cited

U.S. PATENT DOCUMENTS

| 2012/0203338 A1* | 8/2012 | Jain | .................. A61L 27/34 623/6.62 |
| 2014/0074074 A1* | 3/2014 | Dick | .................. A61F 9/00825 606/6 |

* cited by examiner

*Primary Examiner* — Jerrah Edwards
*Assistant Examiner* — Christine L Nelson
(74) *Attorney, Agent, or Firm* — Wood, Phillips, Katz, Clark & Mortimer (57) ABSTRACT

An intraocular lens has central lens body with a first and second, opposite posterior and anterior surfaces, the posterior and anterior surfaces meeting in a rounded peripheral side surface. The lens further has at least a pair of haptics extending from the peripheral side surface of the central lens body, each of the haptics having an arcuate configuration so that a radially distal end of each haptic is engageable within the ciliary sulcus of the eye. The haptics engageable with the ciliary sulcus for stabilizing the central lens body at a location posterior, or rearward, of both the lens capsule anterior and posterior portions, such that the central lens body seals the anterior and posterior portions together proximal to a capsulotomy in each of the anterior and posterior portions.

6 Claims, 6 Drawing Sheets

INTRAOCULAR LENS AND METHODS FOR IMPLANTING THE SAME

FIELD OF THE INVENTION

The present invention relates generally to the field of ophthalmic surgery, and more particularly, to an improved intraocular lens and methods for implanting an improved intraocular lens into the human eye.

BACKGROUND OF THE INVENTION

When the eye becomes aged, diseased, or injured it may be necessary to remove the natural lens of the eye. Such removal is called cataract surgery, in which a lens that has become clouded is removed. The removal of the natural lens of the eye results in the loss or alteration of focused vision of a patient. Therefore, an artificial lens will be necessary to restore the vision of the patient. Some eyes have an oblong, irregularly shaped cornea that causes astigmatism, or blurred vision due to a refractive error in the eye.

Artificial lenses may be provided in eyeglasses, contact lenses, or as a permanent implant known as an intraocular lens (hereinafter "IOL"). The IOL has an artificial, generally circular lens body with one or more stabilizing projections, arms, or haptics extending from the lens body. Special types of lens bodies may be used to correct for various vision problems such as astigmatism, presbyopia, farsightedness or nearsightedness, etc.

To implant the IOL in the eye, an incision is made in the cornea into the anterior chamber of the eye, typically while maintaining positive pressure within the eye to prevent collapse of the delicate structures of the eye. The IOL is generally folded or otherwise placed in a compressed state within an injector housing, The IOL may also be inserted into the eye in an unfolded state dependent upon the flexibility of the IOL material. In the case of an injector, the injector housing is elongate for being placed through the incision and into the patient's cornea after the natural lens and cortex has been disassembled and aspirated from the capsular bag, such as through phacoemulsification or laser assisted surgery. A plunger is retained within the injector housing and is movable with respect to the housing. Movement of the plunger through the housing presses the IOL forward into the eye. The IOL, typically being resilient (with elastic memory), will subsequently expand to an uncompressed state upon entering the eye and exiting the injector. The haptics of the IOL serve to balance and center the IOL within the eye of the patient. The IOL is typically made from biocompatible materials such as PMMA, silicone, hydrogel, or acrylic.

During the removal of the natural lens of the eye, a physician may note that the zonules, or supporting ligaments of the capsular bag which contains the lens, are weakened, deteriorated, or otherwise insufficient to provide adequate structural support to centralize the haptics of the IOL within the eye. Therefore, a capsular tension apparatus or ring may be required to exert an outward pressure on the capsular bag prior to implantation of the IOL. Such capsular tension rings (CTR) are typically generally round or C-shaped and can be provided in various diameters to accommodate variations in human capsular bag diameters. Capsular tension rings are typically formed from a biocompatible implant material such as Polymethyl methacrylate (PMMA), silicone, hydrogels or acrylics. Other materials are also useful, depending upon the configuration of the rings, and how well they maintain their shape, and the size of the intended capsule.

Capsular tension rings may be inserted through an incision in the anterior portion of the eye or may be injected through the incision in a similar fashion as described above with respect to the IOL.

Today, the IOL is typically implanted within the lens capsule (also referred to herein as a "capsular bag" or simply as a "capsule") after the natural lens nucleus and cortex have been removed through a capsulotomy or capsulorhexis of the anterior portion of the lens capsule. This method of implantation inherently relies on the natural strength and positioning of the connective tissue or zonules to fix the location of the IOL within the eye for the rest of the patient's lifetime. With the IOL located within the capsule, lens epithelial cells transform to cause shrinkage and whitening of the remaining anterior portion of the capsule, which is a condition that can promote dislocation of the entire IOL-capsule complex. Furthermore, the currently accepted method leaves the posterior portion of the lens capsule intact, which may serve as a scaffold for residual cortex or lens epithelial cells to multiply and gradually cover the posterior portion of the lens capsule to render it opaque. Opacity of the posterior portion of the lens capsule leads to a secondary cataract and blurred, hazy vision for the patient. Secondary cataract may require a secondary surgical operation or laser to remove or cut the posterior portion of the lens capsule and/or the vitreous of the posterior segment, which may subject the patient to many surgical risks, including floaters, swelling of the center of vision, tears or detachment of the retina that lines the back of the eye, growth of abnormal blood vessels and bleeding, infections, blindness, etc., and other post-operative complications that follow such an event, The goal of this invention is for the patient to have only a single operation to correct the patient's vision over the lifetime of the patient, even for patients that are infants or minors.

SUMMARY OF THE INVENTION

The inventor of the present invention has discovered an improved intraocular lens construction for implantation into a human eye and novel methods for implanting the improved intraocular lens within the human eye.

According to one aspect of the present invention, an intraocular lens is implanted into a human eye having a ciliary sulcus, a lens capsule with an anterior portion and a posterior portion, a natural lens nucleus, a cortex, and an anterior hyaloid membrane. The method includes the step of performing a continuous curvilinear capsulotomy of the anterior portion of the lens capsule. The method further includes the step of removing the natural lens nucleus and cortex from the lens capsule. The method includes the step of polishing the anterior portion and posterior portion of the lens capsule and placing a viscoelastic Ophthalmic Viscosurgical Device (OVD) in the ciliary sulcus to flatten the anterior and posterior portions of the lens capsule together in a substantially horizontal plane. The method includes the step of puncturing a central region of the posterior portion of the lens capsule and instilling a cohesive OVD between the anterior hyaloid membrane and the posterior portion of the capsule to define a space of Berger. The method further includes performing a continuous curvilinear capsulotomy of the posterior portion of the lens capsule and the implantation of the improved intraocular lens so as to locate at least two haptics of the lens within the ciliary sulcus anchored to move with the ciliary muscle and to further locate (i.e. capture) a central lens body of the lens through both of the capsulotomies into the space of Berger.

According to another inventive aspect of the present invention, the inventor has discovered another novel method for implanting an improved intraocular lens within the human eye. The method is performed on a human eye having a ciliary sulcus, a lens capsule with an anterior portion and a posterior portion, the lens capsule with the cortex and the natural lens nucleus substantially removed therefrom, and the lens capsule having a capsulotomy in each of the anterior and posterior portions. The method includes the step of implanting an intraocular lens into the human eye so as to locate at least two haptics of the intraocular lens within the ciliary sulcus and to further locate a central lens body of the intraocular lens through both of the capsulotomies into a space of Berger behind the anterior and posterior portions of the lens capsule.

In accordance with the present invention, an intraocular lens has a generally circular, central lens body having first and second, opposite anterior and posterior surfaces. At least one of these surfaces has an arcuate cross-sectional configuration for providing vision correction for a patient. The posterior and anterior surfaces meet in a rounded peripheral side surface. The lens further includes at least two haptics extending from the peripheral side surface of the central lens body. Each of the at least two haptics has an arcuate configuration so that a radially distal end of each haptic is engageable within the ciliary sulcus of the of the eye for (i) stabilizing the central lens body at a location posterior of both the anterior and posterior portions of the lens, and (ii) sealing the anterior and posterior portions of the lens capsule together proximal to the capsulotomies therein.

Other features and advantages of the present invention will become readily apparent from the following detailed description, the accompanying drawings, and the appended claims. Better understood with reference to the accompanying figures and detailed description.

BRIEF DESCRIPTION OF THE DRAWINGS

FIG. 5 is a top plan diagrammatic view of the intraocular lens shown in FIG. 3 implanted within the human eye, and FIG. 5 shows the central lens body tucked beneath the anterior portion of the lens capsule and the lens haptics located within the ciliary sulcus;

FIG. 6 is side elevation diagrammatic view of the intraocular lens shown in FIG. 3 implanted within the human eye, and FIG. 6 shows the haptics of the intraocular lens located within the ciliary sulcus and the lens body located rearward of the lens capsule anterior and posterior portions;

FIG. 7 is another side elevation diagrammatic view of the intraocular lens shown in FIG. 3 implanted within the human eye, however FIG. 7 shows the haptics hidden for illustrative purposes only.

DETAILED DESCRIPTION OF THE PREFERRED EMBODIMENTS

While the present invention is susceptible of embodiment in various forms, there is shown in the drawings and will hereinafter be described a presently preferred embodiment of the invention, with the understanding that the present disclosure is to be considered an exemplification of the invention, and is not intended to limit the invention to the specific embodiment illustrated.

Figure 1:
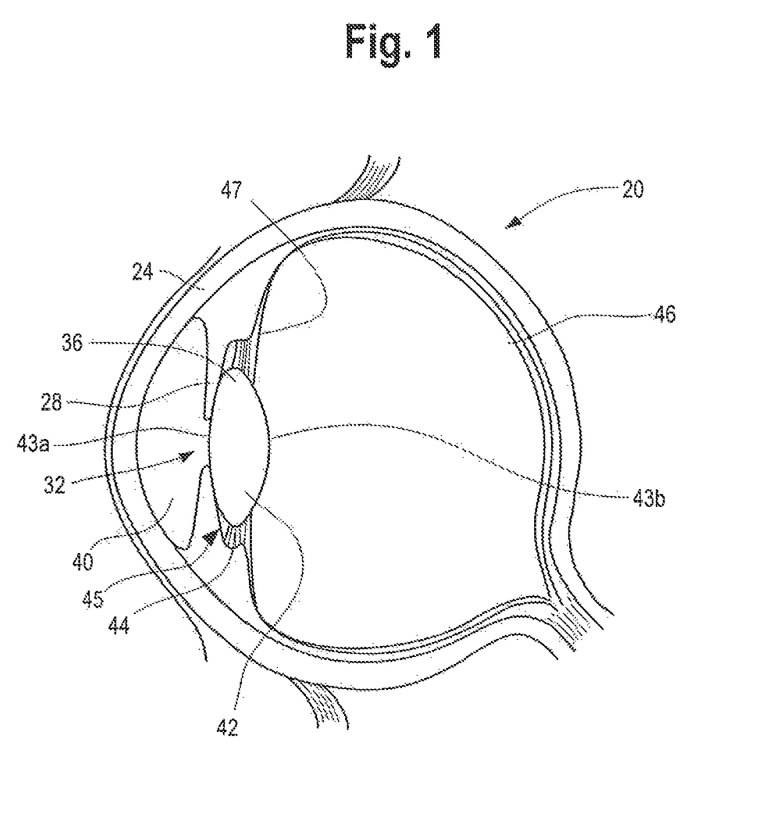
FIG. 1 is a cross-sectional, diagrammatic view of a human eye
Figure 2:
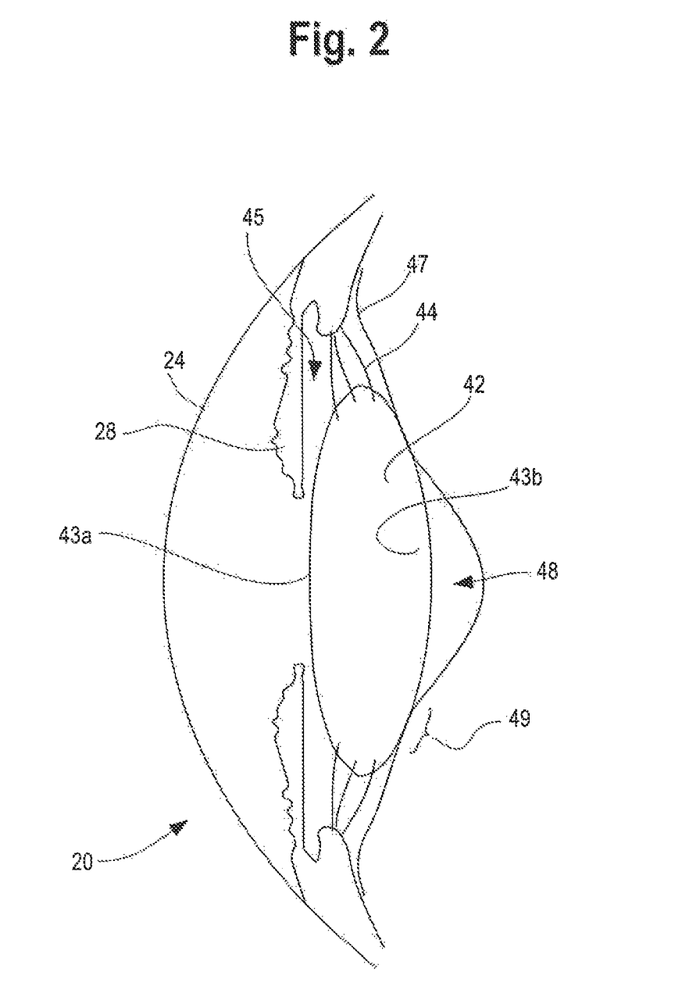
FIG. 2 is an enlarged, cross-sectional diagrammatic view of the anterior segment of the human eye.

FIGS. 1 and 2 show a diagrammatic cross-sectional view of the human eye 20. Beginning at the exterior of the eye 20, the eye 20 has a protective outer layer or cornea 24 which retains the fluids or aqueous humor of the eye 20 and which focuses light. Inward of the cornea 24 is the ring-like iris 28 with an aperture or pupil 32 for restricting light reaching the lens 36. The lens 36 defines the posterior extent of the anterior segment 40 of the eye 20, sitting behind the iris 28. The lens 36 is composed of protein encased in a capsular bag 42. Supporting ligaments or zonules 44, composed of 360 degrees of attachments anterior, equatorial, and posterior, and together with Wieger's ligament (49 in FIG. 2) which defines the space of Berger (48 in FIG. 2), stabilize and center the capsular bag 42 within the eye 20. Opposing the anterior segment 40 of the eye 20 is the posterior segment 46 containing the vitreous body, optic nerves, veins, and arteries of the eye 20. The capsular bag 42 has a forward or anterior wall or portion 43a and a rearward or posterior wall or portion 44b that together retain the denser, hard lens nucleus and the surrounding, less dense lens cortex. A crevice or sulcus 45 exists between the iris 28 and the zonules 44. The anterior hyaloid membrane 47 is located behind the capsular bag 42 and separates the vitreous humor of the eye from the anterior segment 40.

Figure 3:
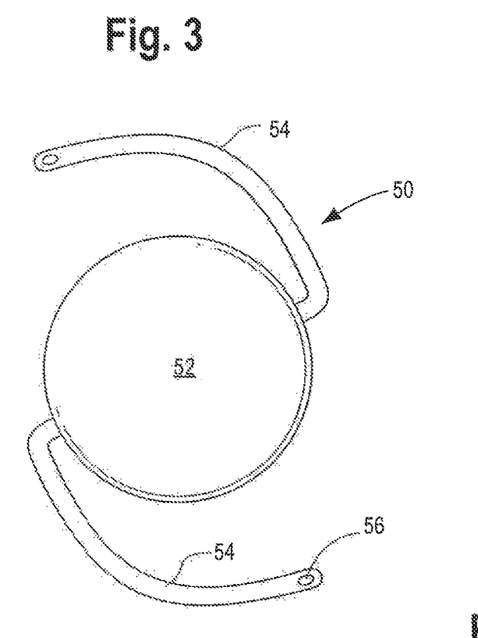
FIG. 3 is a top plan view of an improved intraocular lens according to the present invention.
Figure 4:
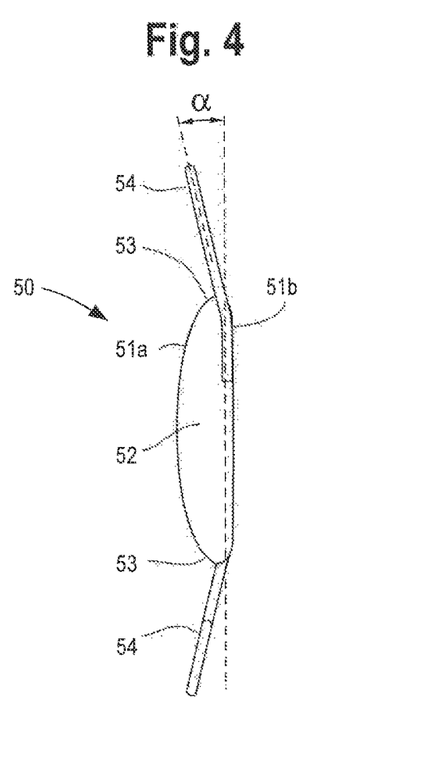
FIG. 4 is a side elevation view of the intraocular lens shown in FIG. 3.

FIGS. 3 and 4 show an improved intraocular lens (IOL) 50 embodying the principles of the present invention. Attendant to a phacoemulsification procedure for removal of the natural lens nucleus and cortex from the capsular bag 42, the IOL 50 is especially suited for the implantation technique that will be discussed in detail hereinafter, The lens 50 is made from a biocompatibie material such as PMMA, silicone, hydrogel, or acrylic either hydrophobic or hydrophilic or a combination thereof, and has a central lens body 52 having first and second, opposite anterior (anterior with respect to the frontal plane) and posterior (posterior with respect to the frontal plane) surfaces 51a and 51b, respectively. At least one of these surfaces 51a and 51b has an accurate cross-sectional configuration for providing vision correction for the patient.

Referring to FIG. 3, the anterior surface 51a and posterior surface 51b of the central lens body 52 meet or join in a rounded peripheral side surface 53, preferably at about a 90-degree angle. As will be discussed in detail hereinafter, the peripheral side surface 53 is especially suited for engaging the posterior portion 43b of the capsular bag 42. To this end, the rounded peripheral side surface 53 may be treated with a surface treatment or applied layer of a different material, or made from a material that is different from the remaining portion of the lens body 52 to enhance sealing of the peripheral side surface 53 with the posterior portion 43b of the capsular bag 42.

The lens body 52 may have one or more surfaces of a varying degree of convexity depending on the need for correction to the patient's vision. The lens body 52 may have a toric or spherical shape, a positive dioptric power, or possess multiple focal points to correct a patient's vision as is known in the art. Preferably, the lens body 52 includes or is treated with an ultraviolet radiation-blocking chromophore, and it may be especially desirable that the chromophore includes a blue-filtering chromophore to absorb harmful wavelengths of light.

Referring to FIGS. 3 and 4, the lens 50 further preferably includes a pair of haptics 54 extending from the central lens body 52 generally at diametrically opposed portions thereof. Each of the haptics 54 has an arcuate, elongated configuration so that an outwardly facing or distal surface of each haptic is engageable with the sulcus 45 for stabilizing the lens 50 and limiting relative movement therebetween. The two generally arcuate haptics 54 extend generally radially outward from the exterior surface of the lens body 52, and preferably are angulated with respect to the central lens body 52 by an angle α of between 5-15 degrees (FIG. 4). While there are only two haptics 54 illustrated on the preferred embodiment of the lens 50, it will be appreciated that more haptics 54 may be employed, or more points of contact with the lens body 52 may be required, in order to retain the lens body 52 at a central location within the eye and possibly allow for anterior-posterior articulation based on fixation to ciliary muscle movement upon accommodation.

With reference to FIG. 3, the haptics 54 each have an eyelet 56 formed near the distal portion thereof, The eyelets 56 may be used for fixation of the haptics 54 within the eye. One or both of the haptics 54 may include a hinge or living hinge connecting between the lens body 52 and the distal portion of the haptic 54. The haptics 54 are preferably formed from a polyvinylidene difluoride (PVDF) and have an elongate, curved shape.

Figure 5:
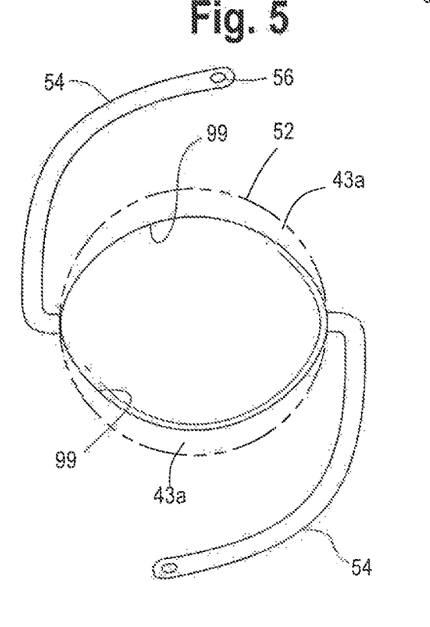
Figure 6:
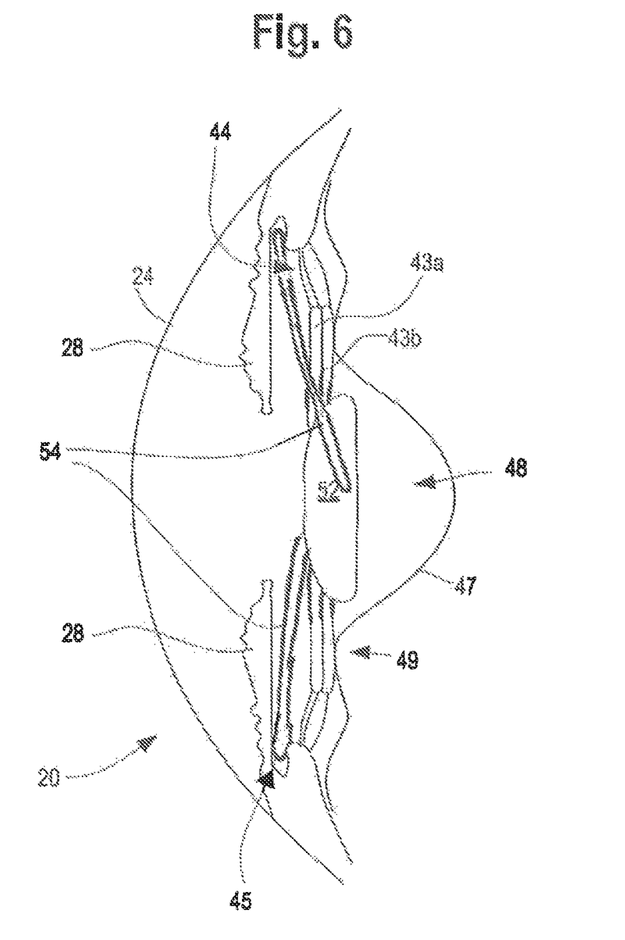
Figure 7:
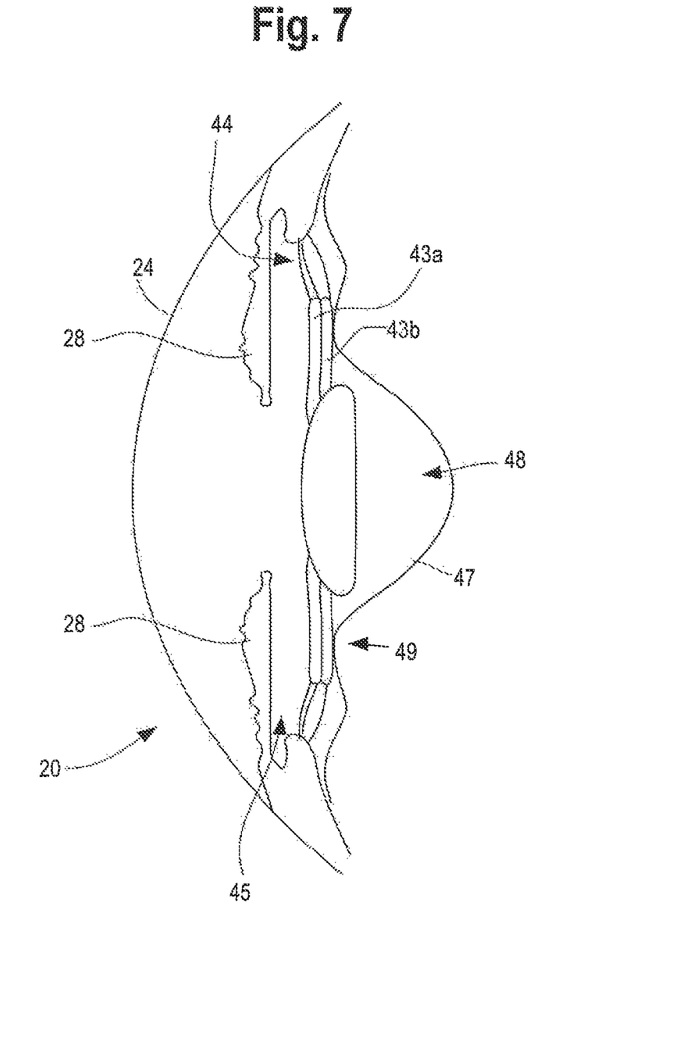
Figure 8:
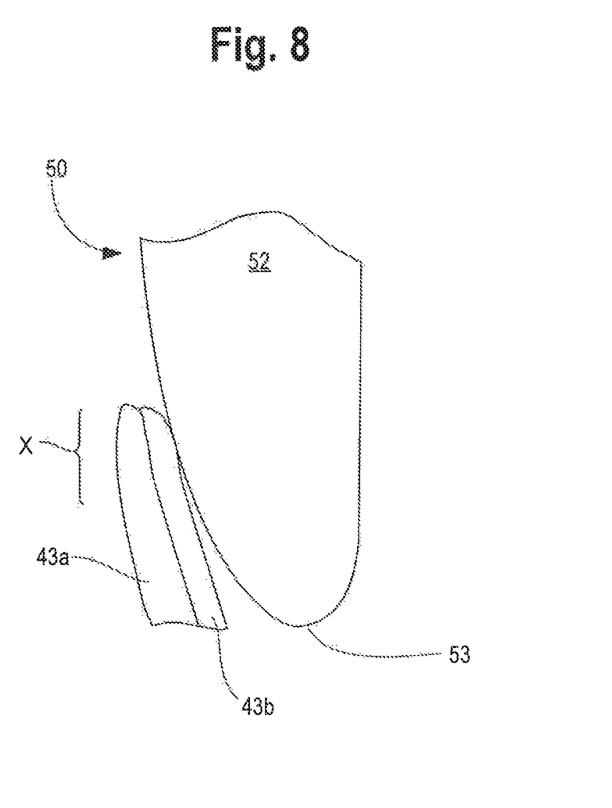
FIG. 8 is a greatly enlarged, side elevation diagrammatic view of just the central lens body in contact with the lens capsule anterior and posterior portions.

The inventor of the present invention has discovered that it would be beneficial to provide an improved intraocular lens which is desirably configured to for implantation such that (i) the haptics 54 reside in the sulcus 45, and (ii) the lens body 52 resides rearward of the capsular bag 42, which will be discussed in detail hereinafter. Such an improved intraocular lens may capture the optic through both a capsulotomy in the anterior portion 43a of the capsule 42 and a capsulotomy in the posterior portion 43b of the capsule 42, such that a leading edge (99 in FIG. 5) of the anterior portion 43a and the posterior portion 43b overlap or extend beyond the periphery of the central lens body 52 by about a dimension "X" (FIG. 8) of about 1 mm for substantially 360 degrees (except for the optic-haptic junction). In this manner, secondary cataract of the posterior portion 43b of the lens capsule 42 may be prevented, and lens capsule shrinkage and fibrosis may be prevented, such that duplicative or remedial surgeries common with current surgical procedure and lens design may be minimized or prevented over the lifetime of the patient.

An inventive method of implantation and operation of the inventive lens 50 will now be discussed. After one or more incisions have been made in the cornea 24, the physician will perform a continuous curvilinear capsulotomy (CCC) of the anterior portion 43a of the lens capsule 42. Preferably, a 5 mm aperture is created by this CCC. The natural lens nucleus and cortex are removed from the lens capsule 42 by any conventional or special means such as by pre-chop of the nucleus, phacoemulsification of the nucleus or segmentation by laser, and aspiration of the nucleus and the cortex. The anterior portion 43a and the posterior portion 43b of the lens capsule 42 are then polished by any suitable conventional or special vibratory tip, irrigating tip, or curette.

The inventor has found that it would be preferable to implant, inject, or otherwise place a viscoelastic OVD into the ciliary sulcus 45 to flatten both the anterior portion 43a and the posterior portion 43b of the lens capsule 42 together in a substantially horizontal plane.

The inventor has further found that it would be preferable to lift up/forward and puncture a central region of the posterior portion 43b of the lens capsule 42 such as with a 30 g bevel up needle, and to instill a cohesive OVD between the anterior hyaloid membrane 47 and the posterior portion 43b of the lens capsule 42 to define a Berger's space 48 up to Wieger's ligament 49 to prevent rupture of the anterior hyaloid membrane 47 and subsequent vitreous loss. The inventor believes that it may be possible with automated, rather than manual means, to perform the step of opening the posterior capsule. The physician will perform a CCC of the posterior portion 43b of the lens capsule 42. Preferably, a 5 mm aperture is created by this CCC. The posterior CCC may be done manually, by a femtosecond laser sterile re-docking off label, with a precision pulse Zepto device available from Mynosys, or other conventional or special methods.

With reference to FIGS. 5-8, the inventor has found that it would be preferable to implant the lens 50 within the eye so as to locate the two haptics 54 within the ciliary sulcus 45 between the iris 28 and the zonules 44, causing it to anchor to the ciliary muscle to effect accommodative movement, and then to further push the central lens body rearward or posteriorly through both of the capsulotomies in the lens capsule 42 into the Berger's space 48 in front of the intact anterior hyaloid membrane 47. In this manner, the anterior portion 43a and posterior portion 43b are tucked over the anterior surface 51a and/or the peripheral side surface 53 (depending on the size of the capsulotomies), for all of the circumference of the central lens body 52 except at two locations substantially 180 degrees apart at the optic-haptic junction where the two haptics 54 extend from the lens body 52 capturing the lens body 52 into Berger's space 48 to give an overall cat-eye appearance of the lens 50 implanted in the eye 20.

It is the inventor's understanding that with the anterior and the posterior portions 43a, 43b of the capsular bag 42 sealed together in this manner, the incidence of visual axis opacity and secondary cataract is minimized or prevented even in pediatric patients, because the lens epithelial cells lack access to the retro-lenticular space behind the capsular bag 42.

It is believed that the lens 50 may be more stable than conventional lens implantation except in the anterior-posterior plane based on ciliary muscle movement because the central lens body 52 stents or prevents appreciable shrinkage of the CCC which contain the anterior and the posterior portions 43a, 43b of the capsular bag 42 sealed together. Additionally, this seal prevents lens material access to the immune system, as any proliferating cells within the capsular bag 42 remain confined to the equatorial region within the capsular bag 42, thus yielding a quieter eye with fewer complications after surgery as shown by Soemmering's ring in the Bag-in-the-Lens prior art technique. With this method, the fit of the lens 50 within the sulcus 45 determines and controls the stability, unlike the Bag-in-the-Lens prior art technique that is dependent upon the zonules 44 and a centered capsulotomy. Further, the inventor believes that this method promotes a flexible and clear capsular bag 42 from equator-to-equator because the lens epithelial cells lack contact to the implanted lens 50 to prevent metaplasia and fibrosis thus possibly allowing accommodative lens movement.

It is believed that the incidence of phimosis and late bag-lens subluxations may decrease or be prevented with this method because anterior capsulotomy is stented by the lens body 52.

The inventor believes that dysphotopsia may decrease or be prevented with this method because the lens body 52 is devoid of sharp or square edges at the peripheral surface 53.

It is believed that the incidence of retinal tear and detachment may decrease with this method because the anterior hyaloid membrane 47 remains intact and need not be disrupted by the treatment of secondary cataract. Further, because the capsule 42 should remain flexible with the hyaloid membrane 47 intact, it is believed that this method may be accommodative.

It is further believed that this method allows for implantation of secondary, or piggyback refractive IOL's typically used for refractive correction in pseudophakic children, because there remains ample space within the sulcus 45. This method may be particularly suitable for refractive lens exchange in adults, as stray light studies have shown that superior vision occurs when the posterior portion 43b of the lens capsule 42 is absent when compared to a polished posterior portion 43b that is left in place.

The inventor anticipates that for patients with congenital cataracts, typically treaded by anterior vitrectomy, that this method will result in less consecutive open angle glaucoma because there is no liberation of vitreal elements to adversely affect the immature trabeculum.

It is believed that if PMMA optics are excluded from the material of the lens 50, which has been shown to cause opacity over time in the vitreous face in babies which is not so of acrylic material in contact with the anterior hyaloid membrane 47.

From the foregoing, it will be observed that numerous modifications and variations can be effected without departing from the true spirit and scope of the novel concept of the present invention. It is to be understood that the present disclosure is to be considered an exemplification of the invention, and is not intended to limit the invention to the specific embodiments illustrated. The disclosure is intended to cover by the appended claims all such modifications as fall with the scope of the claims.

The invention claimed is:

1. A method of implanting an intraocular lens in a human eye having a ciliary sulcus, a lens capsule with an anterior portion and a posterior portion, a natural lens nucleus, a cortex and an anterior hyaloid membrane, the method comprising the steps of:

performing a continuous curvilinear capsulotomy of the anterior portion of the lens capsule;

removing the natural lens nucleus and cortex from the lens capsule;

polishing the anterior portion and posterior portion of the lens capsule;

placing a viscoelastic OVD in the ciliary sulcus to flatten the anterior and posterior portions of the lens capsule together in a substantially horizontal plane;

performing a continuous curvilinear capsulotomy of the posterior portion of the lens capsule; and implanting an intraocular lens in the eye, the intraocular lens having a generally circular, central lens body having first and second, opposite posterior and anterior surfaces, at least one of said surfaces having an arcuate cross-sectional configuration for providing vision correction for the eye, said posterior and anterior surfaces meeting in a rounded peripheral side surface, said central lens body having at least two haptics extending from said peripheral side surface of said central lens body, each of said at least two haptics having an arcuate configuration so that a radially distal end of each haptic is engageable within the ciliary sulcus of the eye for (i) stabilizing said central lens body at a location posterior of both the lens capsule anterior and posterior portions, and (ii) sealing the anterior and posterior portions together proximal to each capsulotomy in said anterior portion and said posterior portion, wherein the step of implanting said lens in the eye includes locating said at least two haptics within the ciliary sulcus and further locating said central lens body through both of said capsulotomies into a Berger's space.

2. The method of claim 1 further comprising the step of puncturing a central region of the posterior portion of the lens capsule and instilling cohesive OVD between the anterior hyaloid membrane and the posterior portion of the capsule in the Berger's space.

3. The method of claim 1 wherein each of the steps of performing a capsulotomy of the anterior and posterior portions of the lens capsule includes making a substantially 5 mm diameter aperture in each of the anterior and posterior portions of the lens capsule.

4. The method of claim 1 wherein the step of implanting said intraocular lens includes capturing said central lens body by pushing said central lens body through both of the capsulotomies to locate said central lens body below the posterior capsule in the Berger's space thereby tucking the posterior portion of the capsule over said central lens body for substantially the full circumference of said lens body except where said haptics extend from said central lens body.

5. The method of claim 1 further comprising the step of sealing together the anterior and the posterior portions of the lens capsule, the anterior and posterior portions of the lens capsule being stretched over the peripheral, side surface of the central lens body.

6. A method of implanting an intraocular lens in a human eye having a ciliary sulcus, a lens capsule with an anterior portion and a posterior portion, the lens capsule with the cortex and the natural lens nucleus substantially removed therefrom, and the lens capsule having a capsulotomy in each of the anterior and posterior portions, the method comprising the step of:

implanting an intraocular lens in the eye, the intraocular lens having a generally circular, central lens body having first and second, opposite posterior and anterior surfaces, at least one of said surfaces having an arcuate cross-sectional configuration for providing vision correction for the eye, said posterior and anterior surfaces meeting in a rounded peripheral side surface, said central lens body having at least two haptics extending from said peripheral side surface of said central lens body, each of said at least two haptics having an arcuate configuration so that a radially distal end of each haptic is engageable within the ciliary sulcus of the eye for (i) stabilizing said central lens body at a location posterior of both the lens capsule anterior and posterior portions, and (ii) sealing the anterior and posterior portions together proximal to each capsulotomy in said anterior portion and said posterior portion, said step of implanting said lens into the human eye includes locating said at least two haptics within the ciliary sulcus and locating said central lens body through both of said capsulotomies into a Berger's space behind the anterior and posterior portions of the lens capsule with an intact anterior hyaloid membrane.

\* \* \* \* \*